United States Patent
Tadanaga et al.

(10) Patent No.: US 12,240,754 B2
(45) Date of Patent: Mar. 4, 2025

(54) LIQUID FOR NITRIDING TREATMENT, NITRIDED METAL OXIDE MANUFACTURING METHOD, AND NITRIDED INDIUM OXIDE FILM

(71) Applicants: NATIONAL UNIVERSITY CORPORATION HOKKAIDO UNIVERSITY, Sapporo (JP); NISSAN CHEMICAL CORPORATION, Tokyo (JP)

(72) Inventors: Kiyoharu Tadanaga, Sapporo (JP); Akira Miura, Sapporo (JP); Tadayuki Isaji, Funabashi (JP); Shinichi Maeda, Funabashi (JP)

(73) Assignees: NATIONAL UNIVERSITY CORPORATION HOKKAIDO UNIVERSITY, Sapporo (JP); NISSAN CHEMICAL CORPORATION, Sapporo (JP)

(*) Notice: Subject to any disclaimer, the term of this patent is extended or adjusted under 35 U.S.C. 154(b) by 998 days.

(21) Appl. No.: 17/266,188

(22) PCT Filed: Aug. 20, 2019

(86) PCT No.: PCT/JP2019/032484
§ 371 (c)(1),
(2) Date: Feb. 5, 2021

(87) PCT Pub. No.: WO2020/040149
PCT Pub. Date: Feb. 27, 2020

(65) Prior Publication Data
US 2021/0292168 A1    Sep. 23, 2021

(30) Foreign Application Priority Data
Aug. 22, 2018 (JP) .................. 2018-155818

(51) Int. Cl.
*C01B 21/082* (2006.01)
*C07D 229/00* (2006.01)

(52) U.S. Cl.
CPC ........ *C01B 21/0821* (2013.01); *C07D 229/00* (2013.01)

(58) Field of Classification Search
CPC ............... C01B 21/0821; C01B 21/06; C07D 229/00; H01L 29/7869; C01G 15/00; C01P 2002/52
See application file for complete search history.

(56) References Cited

U.S. PATENT DOCUMENTS

| | | | |
|---|---|---|---|
| 6,013,758 A * | 1/2000 | Schmid | C08G 69/18 528/323 |
| 2013/0101829 A1* | 4/2013 | Sasaki | B81C 1/0038 977/758 |
| 2017/0073229 A1* | 3/2017 | Kageyama | C30B 31/08 |

FOREIGN PATENT DOCUMENTS

| | | |
|---|---|---|
| JP | 2003-12309 A | 1/2003 |
| JP | 2006-111520 A | 4/2006 |

(Continued)

OTHER PUBLICATIONS

Reyes-Gil et al. "Nitrogen-Doped In2O3 Thin Film Electrodes for Photocatalytic Water Splitting" J. Phys. Chem. C 2007, 111, 14579-14588 (Year: 2007).*

(Continued)

*Primary Examiner* — Wayne A Langel
*Assistant Examiner* — Syed T Iqbal
(74) *Attorney, Agent, or Firm* — Oliff PLC

(57) ABSTRACT

An alkali metal amide is dissolved in a cyclic alkylene urea represented by the formula (1) (wherein each of $R_1$ and $R_2$ represents a C1 to C3 alkyl group, and $R_3$ represents a C1 to C4 alkylene group).

(Continued)

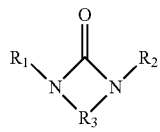

(1)

6 Claims, 1 Drawing Sheet

(56) References Cited

FOREIGN PATENT DOCUMENTS

| | | |
|---|---|---|
| JP | 2013-256434 A | 12/2013 |
| JP | 2015-086170 A | 5/2015 |
| JP | 2016-63053 A | 4/2016 |

OTHER PUBLICATIONS

Mukhopadhyay et al. "Substitution of HMPT by Cyclic Urea DMPU as a Cosolvent for highly reactive Nucleophiles and Bases" Helvetica Chimica acta. vol. 65 Fasc. 1 (1982) Nr. 39 p. 385-391 (Year: 1982).*
Apr. 14, 2022 partial Supplementary Search Report issued in European Patent Application No. 19853127.9.
Nov. 5, 2019 International Search Report issued in International Patent Application No. PCT/JP2019/032484.
M. Jansen et al. "Inorganic Yellow-Red Pigments Without Toxic Metals". Nature, vol. 404, Apr. 27, 2000, pp. 980-982.
Jennifer C. Hsieh et al. "Ambient Pressure, Low-Temperature Synthesis and Characterization of Colloidal InN Nanocrystals". Journal of Materials Chemistry, vol. 20, No. 8, 2010, p. 1435-1437.
Yi Xie et al. "A Benzene-Thermal Synthetic Route to Nanocrystalline GaN". Science, vol. 272, Jun. 28, 1996, pp. 1926-1927.
Lishan Yang et al. "Sulfur-Assisted Synthesis of Nitride Nanocrystals". Dalton Transactions, vol. 39, 2010, pp. 2855-2860.
Junya Kano et al. "Preparation of GaN Powder by Mechanochemical Reaction Between Ga2O3 and Li3N". Journal of Alloys and Compounds, vol. 464, 2008, pp. 337-339.
Hyoung-Do Kim et al. "Highly Stable Thin-Film Transistors Based on Indium Oxynitride Semiconductor". ACS Applied Materials & Interfaces, Apr. 18, 2018, vol. 10, No. 18, pp. 15873-15879.
Souhei Okazaki et al. "Characteristics of Indium Oxynitride (InOxNy) Epitaxial Thin Films". Lecture Preprints of the 60th JSAP Spring Meeting, 2013, vol. 60, Mar. 11, 2013, pp. 29P-F2-1.
Shinho Cho. "Effects of Rapid Thermal Annealing Temperature on the Properties of Nitrogen-Doped Indium Oxide Thin Films". Journal of Nanoscience and Nanotechnology, Jun. 1, 2017, vol. 17, No. 6, pp. 4048-4051.
Akira Miura. "Development of Methods for Synthesizing Nitrides and Oxynitrides, and Academic Establishment". Lecture Proceedings of 2017 Annual Conference of the Ceramic Society of Japan, Mar. 1, 2017, pp. 2K08A.
Akira Miura et al. "Development of Novel Nitride Synthesis Method From NaNH2 Melt and Oxides". Lecture Preprints of the 28th Fall Meeting of the Ceramic Society of Japan, vol. 28, Sep. 1, 2015, pp. 2K24.
Zhi Yin Lee et al. "Growth Mechanism of Indium Nitride via Sol-Gel Spin Coating Method and Nitridation Process". Surface & Coatings Technology, Dec. 20, 2016, vol. 310, pp. 38-42.
Miura, A., "Low-temperature synthesis and rational design of nitrides and oxynitrides for novel functional material development," Journal of the Ceramic Society of Japan, vol. 125, No. 7, pp. 552-558, 2017.
Okazaki, S. et al., "Physical properties of indium oxynitride (InOxNy) epitaxial thin films," Lecture Preprints of the 60th JSAP Spring Meeting, Mar. 27-30, 2013, vol. 60, pp. 6-187.
Jul. 18, 2022 extended Search Report issued in European Patent Application No. 19853127.9.

* cited by examiner

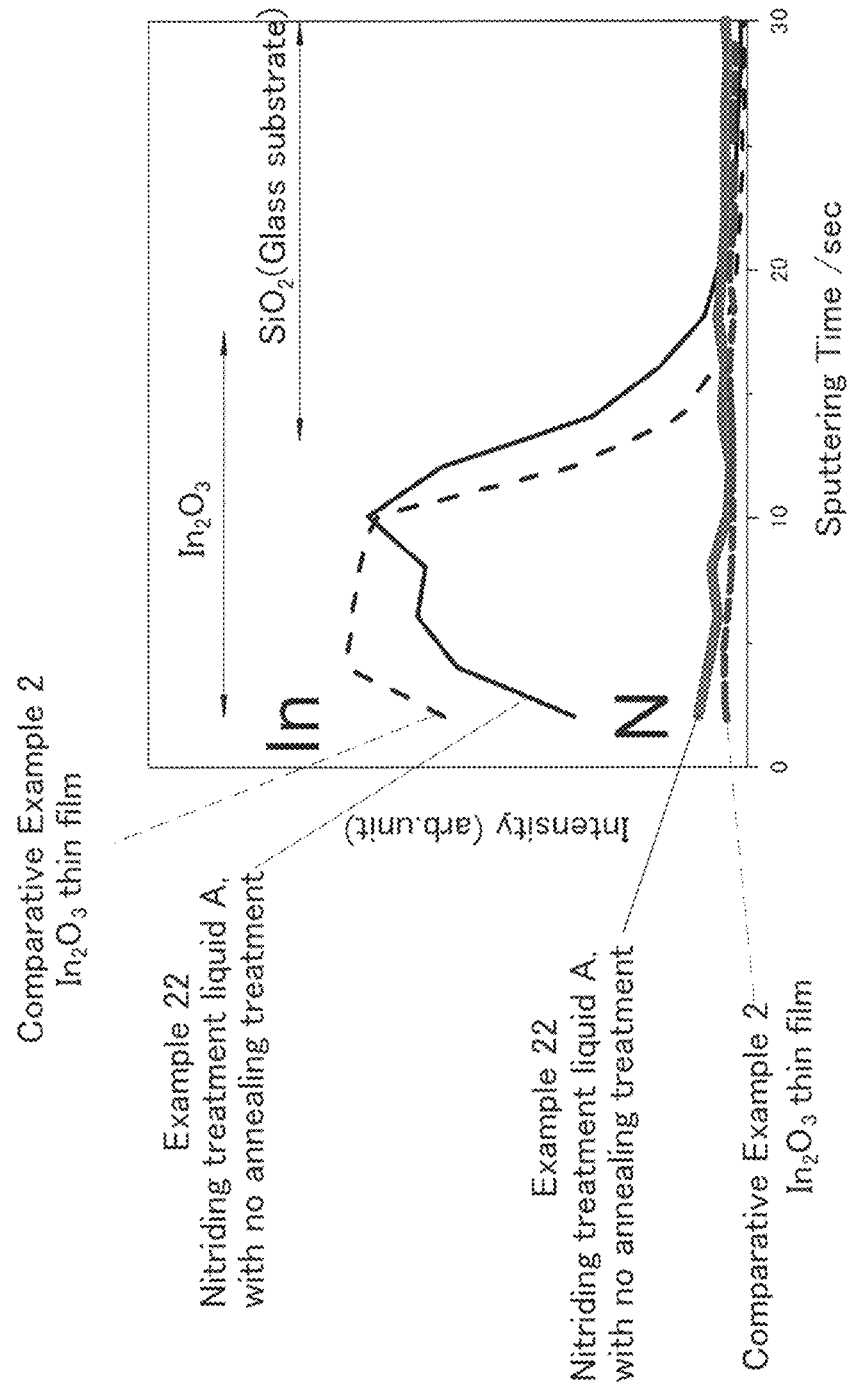

LIQUID FOR NITRIDING TREATMENT, NITRIDED METAL OXIDE MANUFACTURING METHOD, AND NITRIDED INDIUM OXIDE FILM

TECHNICAL FIELD

A fifth mode of the present invention is a specific embodiment of the nitrided metal oxide production method of the fourth mode, wherein the method further includes, after the nitriding step, an annealing step of annealing the metal oxide which is treated by heating in a deoxygenated atmosphere.

BACKGROUND ART

Metal oxides are corrosion-resistant materials having excellent characteristics including high stability, low price, and low toxicity. Thus, metal oxides are widely used as staring materials for producing N-doped metal oxides, metal oxynitrides, and metal nitrides.

For nitriding a metal oxide, the metal oxide must be reduced and nitrided. That is, nitridation requires two reaction steps; i.e., oxygen-bond scission and bond formation reaction with nitrogen.

In reductive nitridation, ammonia gas, nitrogen gas, or a nitrogen-hydrogen gas mixture is used, and reduction with carbon or reaction with lithium nitride is employed. Generally, the process requires a high-temperature treatment at 500 to 1,700° C.

Non-Patent Document 1 discloses synthesis of $Ca_{(1-x)}La_xTaO_{(2-x)}N_{(1+x)}$ from Ca oxide, La oxide, and Ta oxide as starting materials with nitridation in an ammonia gas flow at 700 to 1,000° C.

Patent Document 1 discloses synthesis of (Li,Ga) (O,N) by nitriding an oxide sol containing Li and Ga (i.e., starting material) in an ammonia gas flow at 700 to 1,000° C.

Patent Document 2 and Non-Patent Documents 2 to 5 report synthesis of a nitride at <500° C. by use of a chloride, an amide, etc.

Specifically, in the synthesis of Patent Document 2, an amide compound and a metal and/or compound including a group 13 element are heated in inert gas at 400 to 500° C., to thereby synthesize a nitride.

In Non-Patent Document 2, indium nitride is synthesized by heating an indium halide and an amide compound in an organic medium.

In Non-Patent Document 3, gallium chloride and lithium nitride are heated in benzene, whereby indium nitride is synthesized.

In Non-Patent Document 4, various metals are reacted with sulfur, and sodium azide or sodium amide at 500° C. or lower, to thereby synthesize nitrides.

In Non-Patent Document 5, gallium nitride is synthesized through mechanochemical reaction of gallium oxide with lithium nitride by means of a planet ball mill.

However, according to the aforementioned conventional production methods, metal oxynitrides are synthesized by means of an ammonia gas flow at 700° C. or higher, and the products are thermodynamically unstable. Thus, the conventional production methods have the following problems. Specifically, the treatment at considerably high temperature requires a large amount of energy. In addition, ammonia gas must be handled with care due to its toxicity, and requires a particular treatment such as neutralization in waste treatment. Furthermore, only a limited amount of the ammonia gas flow can be utilized in the reaction, thereby lowering utilization efficiency. Needless to say, since the production methods involve decomposition of ammonia, the reaction must be kinetically controlled.

In order to solve the aforementioned problems, there is proposed a method for producing a metal oxynitride by reacting a metal oxide with an alkali metal amide and a hydride at the melting point of the alkali metal amide or higher (see, for example, Patent Document 3).

Meanwhile, there is need for improving the bias stress stability (reliability) of a thin-film transistor employing a metal oxide semiconductor. Thus, instead of using an IGZO formed through sputtering, trials have been conducted for using a metal oxide thin film such as an indium oxide thin film (see, for example, Patent Document 4).

When the approach of nitriding treatment is employed so as to improve characteristics of indium oxide thin film, the indium oxide film, having poor resistance to alkali, is broken via dissolution in the molten sodium amide used in the production method of Patent Document 3, which is one problem. In this case, nitridation fails to be completed, which is problematic. Also, according to the method of Patent Document 3, the alkali metal amide is used in a molten state at its melting point or higher. Since sodium amide may ignite in air, the method must be carried out under protective conditions including an inert gas atmosphere, which makes the method considerably cumbersome.

PRIOR ART DOCUMENTS

Patent Documents

Patent Document 1: Japanese Patent Application Laid-Open (kokai) No. 2006-111520
Patent Document 2: Japanese Patent Application Laid-Open (kokai) No. 2003-12309
Patent Document 3: Japanese Patent Application Laid-Open (kokai) No. 2013-256434
Patent Document 4: Japanese Patent Application Laid-Open (kokai) No. 2016-63053

Non-Patent Documents

Non-Patent Document 1: Jansen, M. & Letschert, H. P. Inorganic yellow-red pigments without toxic metals. Nature 404, 980-982 (2000).
Non-Patent Document 2: Hsieh, J. C., Yun, D. S., Hu, E. & Belcher, A. M. Ambient pressure, low-temperature synthesis and characterization of colloidal InN nanocrystals. J. Mater. Chem. 20 (2010).
Non-Patent Document 3: Xie, Y., Qian, Y., Wang, W., Zhang, S. & Zhang, Y. A Benzene-Thermal Synthetic Route to Nanocrystalline GaN. Science 272, 1926-1927 (1996).
Non-Patent Document 4: Yang, L., Yu, H., Xu, L., Ma, Q. & Qian, Y. Sulfur-assisted synthesis of nitride nanocrystals. Dalton Transactions 39 (2010).
Non-Patent Document 5: Kano, J., Kobayashi, E., Tongamp, W. & Saito, F. Preparation of GaN powder by mechanochemical reaction between Ga2O3 and Li3N. J. Alloys Compd. 464, 337-339 (2008).

SUMMARY OF THE INVENTION

Problems to be Solved by the Invention

In view of the foregoing, an object of the present invention is to provide a nitriding treatment liquid which can achieve relatively easy nitridation of a metal oxide thin film.

Another object is to provide a nitrided metal oxide production method. Still another object is to provide a nitrided indium oxide film.

Means for Solving the Problems

In a first mode of the present invention to attain the aforementioned objects, there is provided a nitriding treatment liquid characterized by comprising an alkali metal amide dissolved in a cyclic alkylene urea represented by the following formula (1):

[F1]

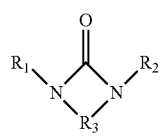

(1)

(wherein each of $R_1$ and $R_2$ represents a C1 to C3 alkyl group, and $R_3$ represents a C1 to C4 alkylene group).

A second mode of the present invention is a specific embodiment of the nitriding treatment liquid of the first mode, wherein the cyclic alkylene urea is dimethylpropylene urea or dimethylethylene urea.

A third mode of the present invention is a specific embodiment of the nitriding treatment liquid of the first or second mode, wherein the alkali metal amide is lithium amide, sodium amide, potassium amide, or a mixture thereof.

In a fourth mode of the present invention, there is provided a nitrided metal oxide production method, characterized by comprising a nitriding step of heating a nitriding treatment liquid as recited in any of the first to third modes in an inert gas atmosphere, while the liquid is in contact with the surface of a metal oxide.

The present invention relates to a liquid for carrying out nitriding treatment (hereinafter referred to as a "nitriding treatment liquid"), to a method for producing a nitrided metal oxide (hereinafter referred to as a "nitrided metal oxide production method") employing the treatment liquid, and to a nitrided indium oxide film. As used herein, the term "nitrided metal oxide" refers to a compound containing oxygen and nitrogen and, in a broad sense, a metal oxynitride. The "nitrided metal oxide" encompasses a nitrogen-containing metal oxide and an oxygen-containing metal nitride.

A sixth mode of the present invention is a specific embodiment of the nitrided metal oxide production method of the fourth or fifth mode, wherein the metal oxide is one species selected from among $In_2O_3$, $Ga_2O_3$, $Al_2O_3$, $TiO_2$, $Fe_2O_3$, $MnO_2$, $WO_3$, $MoO_3$, $Li_2TiO_3$, $Li_2ZrO_3$, $Li_2MoO_4$, $Li_2WO_4$, $Na_2MoO_4$, $LiGaO_2$, $LiInO_2$, $NaGaO_2$, $FeMoO_4$, $MnMoO_4$, $FeWO_4$, $MnWO_4$, $LiInO_2$, and $NaInO_2$, or a mixture of the plurality of the oxides.

A seventh mode of the present invention is a specific embodiment of the nitrided metal oxide production method of any of the fourth to sixth modes, wherein the metal oxide is in the form of indium oxide film formed on a substrate.

In an eighth mode of the present invention, there is provided a nitrided indium oxide film, characterized in that the film is a nitrogen-doped indium oxide film formed on a substrate and exhibits a mobility of 6 to 50 $cm^2/Vs$.

A ninth mode of the present invention is a specific embodiment of the nitrided indium oxide film of the eighth mode, wherein the mobility of the film is 30 to 50 $cm^2/Vs$.

Effects of the Invention

According to the present invention, an alkali metal amide for use in nitridation can be handled in the form of solution. Thus, a nitriding treatment liquid which does not ignite in air can be provided. Also, by using the nitriding treatment liquid of the present invention, a thin film having poor resistance to alkali (e.g., indium oxide film) can be nitrided. Thus, a nitrided metal oxide which exhibits favorable adhesion to a substrate can be provided. Furthermore, the nitrided indium oxide film produced with the nitriding treatment liquid of the present invention exhibits a mobility of 6 to 50 $cm^2/Vs$, which is remarkably higher than conventionally attained mobilities. Thus, the film can be suitably used in a thin-film transistor or the like.

BRIEF DESCRIPTION OF THE DRAWINGS

FIG. 1 A chart of glow discharge optical emission spectrometry, showing nitrogen intensity profiles and indium intensity profiles of indium oxide films of Example 22 and Comparative Example 2.

MODES FOR CARRYING OUT THE INVENTION

Embodiments of the present invention will next be described.

A characteristic feature of the nitriding treatment liquid of the present invention resides in that the liquid contains an alkali metal amide dissolved in a cyclic alkylene urea represented by the following formula (1):

[F2]

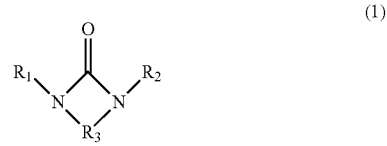

(1)

(wherein each of $R_1$ and $R_2$ represents a C1 to C3 alkyl group, and $R_3$ represents a C1 to C4 alkylene group).

Generally, difficulty is encountered in handling of alkali metal amides in air. However, when an alkali metal amide is dissolved in a cyclic alkylene urea serving as a solvent so as to yield a nitriding treatment liquid, the liquid can be easily handled. As a result, nitriding treatment can be easily performed.

Examples of preferred cyclic alkylene ureas include N,N-dimethylpropyleneamide or N,N-dimethylethyleneamide.

Examples of the alkali metal amide include lithium amide, sodium amide, potassium amide, and a mixture thereof.

No particular limitation is imposed on the alkali metal amide concentration, so long as the amide can be dissolved in the cyclic alkylene urea. The concentration is about 1 mM to about 1,000 mM, preferably about 10 mM to about 500 mM.

In use, the nitriding treatment liquid of the present invention is brought into contact with the surface of metal oxide and subjected to heat treatment in an inert gas atmosphere, whereby the metal oxide is nitrided. The nitriding treatment liquid is in the form of solution in which the alkali amide is dissolved in the cyclic alkylene urea. Thus, the liquid does not ignite in air and can also be used in nitridation of a metal oxide having poor resistance to alkali.

Next will be described the nitrided metal oxide production method employing the nitriding treatment liquid of the present invention.

The nitrided metal oxide production method of the present invention includes a nitriding step of heating the nitriding treatment liquid of the present invention in an inert gas atmosphere, while the treatment liquid is in contact with the surface of a metal oxide.

The metal oxide which may be used in the present invention may be a binary oxide or a complex oxide. Specific examples of the metal oxide include $In_2O_3$, $Ga_2O_3$, $Al_2O_3$, $TiO_2$, $Fe_2O_3$, $MnO_2$, $WO_3$, $MoO_3$, $Li_2TiO_3$, $Li_2ZrO_3$, $Li_2MoO_4$, $Li_2WO_4$, $Na_2MoO_4$, $LiGaO_2$, $LiInO_2$, $NaGaO_2$, $FeMoO_4$, $MnMoO_4$, $FeWO_4$, $MnWO_4$, $LiInO_2$, $(In_9,Sn_1)_2O_3$, and $NaInO_2$.

The metal oxide may be in the form of granules or thin film. The nitrided metal oxide may be an oxynitride (in a broad sense) encompassing a state of N-doped metal oxide, or an oxynitride (in a narrow sense) in which oxygen and nitrogen are bound to metal.

The process "bringing the nitriding treatment liquid into contact with the surface of metal oxide" refers to causing the nitriding treatment liquid to be deposited on the surface of metal oxide. Specifically, contact of the nitriding treatment liquid with the surface of metal oxide may be achieved by immersing a metal oxide in the nitriding treatment liquid of the present invention and optionally removing the metal oxide after immersion, or spraying or applying the nitriding treatment liquid onto the surface of the metal oxide.

The "nitriding step of heating the nitriding treatment liquid, while the liquid is in contact with the surface of a metal oxide" may be performed at 200° C. to 400° C., preferably 200° C. to 300° C. The heating time may be about 1 to about 50 hours and is preferably 5 to 30 hours.

The inert gas which forms the inert gas atmosphere may be nitrogen or noble gas, with nitrogen or argon being preferred.

The nitriding step (heat treatment) may be performed at ambient pressure or under pressurized conditions. Specifically, the pressure is preferably 20 to 0.1 MPa, more preferably 5 to 0.1 MPa, still more preferably 2 to 0.1 MPa. When the pressure is 20 MPa or higher, care must be taken in handling, and cost for production apparatus increases.

Preferably, the nitrided metal oxide production method of the present invention includes, after the nitriding step, an annealing step of annealing the treated metal oxide by heating in a deoxygenated atmosphere. By performing the annealing step, nitriding treatment can be consistently completed.

In the case where the initial mobility is 2 to 4 $cm^2/Vs$, the mobility increases to 6 to 10 $cm^2/Vs$ after the nitriding step. When the annealing step is performed, the mobility increases to about 20 to about 50 $cm^2/Vs$.

As used herein, the term "deoxygenated atmosphere" refers to a vacuum state containing no oxygen, or an inert gas atmosphere. The vacuum state is, for example, a reduced pressure of 1 Pa or lower, preferably 0.1 Pa or lower. The inert gas which forms the inert gas atmosphere may be nitrogen or noble gas, with nitrogen being preferred.

The heating temperature in the annealing is 200° C. to 500° C., preferably 250° C. to 400° C., and the treatment time is 30 minutes to 10 hours, preferably 1 hour to 5 hours.

The present invention is particularly meritorious in nitriding treatment of a metal oxide film for use in a metal oxide semiconductor thin-film transistor. The thickness of the metal oxide thin film is 50 nm to 100 nm.

By use of the nitriding treatment liquid of the present invention, nitriding treatment of a metal oxide thin film, in particular a metal oxide thin film having poor resistance to alkali, can be performed at high efficiency, whereby the mobility, carrier density, specific resistivity, etc. of the thin film can be enhanced.

Particularly, by carrying out the annealing step after the nitriding step, the mobility, carrier density, specific resistivity, etc. of the thin film can be further enhanced.

Among the nitrided metal oxide thin films produced through the nitrided metal oxide production method of the present invention, a nitrided indium oxide film is particularly a novel product having unique characteristics.

That is, an N-doped indium oxide film formed on a substrate is a completely novel product.

The aforementioned nitrided indium oxide film has a mobility of 6 to 50 $cm^2/Vs$, preferably 30 to 50 $cm^2/Vs$, which has not been attained.

The carrier density of the oxide film is $1 \times 10^{16}$ to $1 \times 10^{19}$ $cm^{-3}$, and the specific resistivity thereof is 0.05 to 100 Ω·cm.

Such a nitrided indium oxide film can be suitably used as a thin-film transistor or the like.

The present invention will next be described in more detail by way of example.

[Measurement Procedure]

(Procedure of Forming $In_2O_3$ Film-Attached Glass Substrate)

$In(NO_3)_3 \cdot 3H_2O$ (2.95 g) was added to 2-propanol (20 g), and the mixture was stirred for 10 hours. Subsequently, acetic acid (0.8 g) and polyethylene glycol (0.9 g) were added to the mixture, and the resultant mixture was stirred for 2 hours, to thereby prepare a precursor solution. Then, a glass substrate (dimensions: 76×26×1.0 (mm)) was immersed in the precursor solution and vertically pulled up from the solution, whereby a thin layer of the precursor solution was uniformly formed on the glass substrate. Subsequently, the glass substrate was heated at 100° C. for 15 minutes, to thereby form a precursor thin film, which was further heated at 500° C. for 2 hours, whereby a uniform $In_2O_3$ thin film was formed. In the Examples of the present invention, all $In_2O_3$ thin film-attached glass substrates were produced through the above procedure.

(Procedure of Determining Film Thickness)

The thickness of each $In_2O_3$ thin film was measured through observation under a scanning electron microscope JEOL JSM-6500F (product of JEOL Ltd.). Specifically, the thickness was determined from a fracture surface of the polished film sample.

(Procedure of Glow Discharge Optical Emission Spectrometry (GDOES))

The nitrogen amount of each nitrided substrate was determined by means of JY5000RF (product of Horiba Ltd.). The measurement was performed at a pressure of 600 Pa, an output of 35 W, a duty cycle of 0.1, and a frequency of 100 Hz.

(Procedure of Determining Carrier Type, Specific Resistivity, Carrier Concentration, and Mobility)

The carrier type, specific resistivity, carrier concentration, and mobility of each of the $In_2O_3$ thin films and nitrided substrates were determined by means of a specific resistivity/Hall coefficient measuring system ResiTest8300 (product of Toyo Corporation).

EXAMPLES (Nitriding Treatment Liquids)

Example 1: Nitriding Treatment Liquid A

Under Ar, sodium amide (0.03 g) was added to N,N'-dimethylpropylene urea (7 mL), and the mixture was stirred at room temperature for 15 minutes. The resultant supernatant was transferred to another vessel, to thereby prepare treatment liquid A. The liquid was found to have a sodium amide concentration of about 15 mM.

Example 2: Nitriding Treatment Liquid B

Under Ar, sodium amide (0.01 g) was added to N,N'-dimethylpropylene urea (7 mL). The mixture was stirred for 24 hours, while the liquid temperature was maintained at 60° C., to thereby prepare treatment liquid B. The liquid was found to have a sodium amide concentration of about 36 mM.

Example 3: Nitriding Treatment Liquid C

Under Ar, sodium amide (0.02 g) was added to N,N'-dimethylpropylene urea (7 mL). The mixture was stirred for 24 hours, while the liquid temperature was maintained at 100° C., to thereby prepare treatment liquid C. The liquid was found to have a sodium amide concentration of about 73 mM.

Example 4: Nitriding Treatment Liquid D

Under Ar, sodium amide (0.05 g) was added to N,N'-dimethylpropylene urea (7 mL). The mixture was stirred for 24 hours, while the liquid temperature was maintained at 150° C., to thereby prepare treatment liquid D. The liquid was found to have a sodium amide concentration of about 180 mM.

(Nitrided Metal Oxide Thin Film Production Method)

Example 11: Nitriding Treatment Method A

Under Ar, $In_2O_3$ thin film (thickness 220 nm)-attached glass substrate and nitriding treatment liquid A (7.0 g) were placed in an autoclave (i.e., a pressure decomposition container) (Product of Yanaco Instrument Development Laboratory, capacity: 70 mL), and the autoclave was tightly closed. The autoclave was heated at 260° C. for 18 hours, whereby the $In_2O_3$ thin film-attached glass substrate was nitrided. Then, the nitrided substrate was removed from the autoclave and washed with a water-ethanol mixture. Subsequently, the nitrided substrate was annealed in vacuum at 300° C. for 1 hour.
(Nitrided Metal Oxide Thin Film Production Method)

Example 12: Nitriding Treatment Method B

The procedure of Example 11 was repeated, except that nitriding treatment liquid B was used instead of nitriding treatment liquid A employed in Example 11, to thereby nitride an $In_2O_3$ thin film-attached glass substrate. Then, the nitrided substrate was removed from the autoclave and washed with a water-ethanol mixture.
(Nitrided Metal Oxide Thin Film Production Method)

Example 13: Nitriding Treatment Method C

The procedure of Example 11 was repeated, except that nitriding treatment liquid C was used instead of nitriding treatment liquid A employed in Example 11, to thereby nitride an $In_2O_3$ thin film-attached glass substrate. Then, the nitrided substrate was removed from the autoclave and washed with a water-ethanol mixture.
(Nitrided Metal Oxide Thin Film Production Method)

Example 14: Nitriding Treatment Method D

The procedure of Example 11 was repeated, except that nitriding treatment liquid D was used instead of nitriding treatment liquid A employed in Example 11, to thereby nitride an $In_2O_3$ thin film-attached glass substrate. Then, the nitrided substrate was removed from the autoclave and washed with a water-ethanol mixture.

Comparative Example 1

Under Ar, $In_2O_3$ thin film (thickness 220 nm)-attached glass substrate and N,N'-dimethylpropylene urea were placed in an autoclave (i.e., a pressure decomposition container) (Product of Yanaco Instrument Development Laboratory, capacity: 70 mL), and the autoclave was tightly closed. The autoclave was heated at 260° C. for 18 hours, whereby the $In_2O_3$ thin film-attached glass substrate was nitrided. Then, the nitrided substrate was removed from the autoclave and washed with a water-ethanol mixture. Subsequently, the nitrided substrate was annealed in vacuum at 300° C. for 1 hour.
(Nitrided Indium Oxide Thin Film)

Example 21: Nitrided Indium Oxide Thin Film A-1

A nitrided substrate was produced through the same procedure as employed in "Nitriding treatment method A" of Example 11. The carrier type, specific resistivity, carrier density, and mobility of the substrate were determined through the aforementioned methods. The carrier type, specific resistivity, carrier density, and mobility were type N, 3 Ωcm, $7\times10^{16}$ $cm^{-3}$, and 40 $cm^2$/Vs, respectively.

Example 22: Nitrided Indium Oxide Thin Film A-2

The procedure of "Nitriding treatment method A" of Example 11 was repeated, except that annealing in vacuum at 300° C. for 1 hour was omitted, to thereby produce a nitrided substrate. The nitrogen amount of the nitrided substrate was determined through GD-OES. FIG. 1 shows the results. Also, the intensity ratio (N/In) of emission attributed to indium to that attributed to nitrogen is shown in Table 1. The intensity corresponds to an intensity value integrated during a sputtering time of 4 to 10 (sec). The carrier type, specific resistivity, carrier density, and mobility of the substrate were determined through the aforementioned methods. The carrier type, specific resistivity, carrier density, and mobility were type N, 0.1 Ωcm, $7\times10^{18}$ $cm^{-3}$, and 9 $cm^2$/Vs, respectively.

Example 23: Nitrided Indium Oxide Thin Film B

A nitrided substrate was produced through the same procedure as employed in "Nitriding treatment method B" of Example 12. The nitrogen amount of the nitrided substrate was determined through GD-OES. The intensity ratio (N/In) of emission attributed to indium to that attributed to nitrogen is shown in Table 1. The intensity corresponds to an intensity value integrated during a sputtering time of 4 to 10 (sec). The carrier type, specific resistivity, carrier density, and mobility of the substrate were determined through the aforementioned methods. The carrier type, specific resistivity, carrier density, and mobility were type N, 0.07 Ωcm, $6\times10^{18}$ cm$^{-3}$, and 20 cm$^2$/Vs, respectively.

Example 24: Nitrided Indium Oxide Thin Film C

A nitrided substrate was produced through the same procedure as employed in "Nitriding treatment method C" of Example 13. The nitrogen amount of the nitrided substrate was determined through GD-OES. The intensity ratio (N/In) of emission attributed to indium to that attributed to nitrogen is shown in Table 1. The intensity corresponds to an intensity value integrated during a sputtering time of 4 to 10 (sec).

Example 25: Nitrided Indium Oxide Thin Film D

A nitrided substrate was produced through the same procedure as employed in "Nitriding treatment method D" of Example 14. The nitrogen amount of the nitrided substrate was determined through GD-OES. The intensity ratio (N/In) of emission attributed to indium to that attributed to nitrogen is shown in Table 1. The intensity corresponds to an intensity value integrated during a sputtering time of 4 to 10 (sec).

Example 26: Nitrided Indium Oxide Thin Film B-2

A nitrided substrate was produced through the same procedure as employed in "Nitriding treatment method B" of Example 12. The substrate was annealed in vacuum at 300° C. for 1 hour. The carrier type, specific resistivity, carrier density, and mobility of the thus-treated substrate were determined through the aforementioned methods. The carrier type, specific resistivity, carrier density, and mobility were type N, 2 Ωcm, $7\times10^{16}$ cm$^{-3}$, and 40 cm$^2$/Vs, respectively.

Comparative Example 2

An In$_2$O$_3$ thin film-attached glass substrate was not subjected to nitriding treatment, and the nitrogen amount of the nitrided substrate was determined through GD-OES. FIG. 1 shows the results. Also, the intensity ratio (N/In) of emission attributed to indium to that attributed to nitrogen is shown in Table 1. The intensity corresponds to an intensity value integrated during a sputtering time of 4 to 10 (sec).

The carrier type, specific resistivity, carrier density, and mobility of the thus-treated substrate were determined through the aforementioned methods. The carrier type, specific resistivity, carrier density, and mobility were type N, 6 Ωcm, $7\times10^{17}$ cm$^{-3}$, and 2 cm$^2$/Vs, respectively.

Comparative Example 3

A nitrided substrate was produced through the same procedure as employed in Comparative Example 1. The carrier type, specific resistivity, carrier density, and mobility of the substrate were determined through the aforementioned methods. The carrier type, specific resistivity, carrier density, and mobility were type N, 0.2 Ωcm, $7\times10^{19}$ cm$^{-3}$, and 3 cm$^2$/Vs, respectively.

Comparative Example 4

The procedure of Comparative Example 1 was repeated, except that annealing in vacuum at 300° C. for 1 hour was omitted, to thereby produce a nitrided substrate. The carrier type, specific resistivity, carrier density, and mobility of the substrate were determined through the aforementioned methods. The carrier type, specific resistivity, carrier density, and mobility were type N, 0.5 Ωcm, $4\times10^{18}$ cm$^{-3}$, and 4 cm$^2$/Vs, respectively.

SUMMARY

FIG. 1 shows the results of comparison of the nitrided indium oxide thin film of Example 22 with the nitrided indium oxide thin film of Comparative Example 2. As shown in FIG. 1, only a feeble intensity of the signal attributed to nitrogen was observed in Comparative Example 2, indicating that no nitridation occurred. In contrast, the nitrided indium oxide thin film of Example 22 exhibited a lower intensity of the signal attributed to indium and a higher intensity of the signal attributed to nitrogen, as compared with Comparative Example 2. Thus, nitridation was found to occur in Example 22.

The above are supported by the N/In signal ratios shown in Table 1. As compared with Comparative Example 2, signal ratios of Examples 21 to 25 were considerably enhanced. Thus, occurrence of substantial nitridation was proven.

Also, Examples 21 and 22 were compared with Comparative Examples 2, 3, and 4 in terms of mobility. In Examples 21 and 22, employing nitriding treatment liquid A of Example 11, mobility was remarkably enhanced. Conceivably, the enhancement in mobility resulted from nitridation of In$_2$O$_3$ thin film.

Further, Example 21 was compared with Example 22. As a result, a considerable enhancement in mobility was confirmed in Example 21 involving annealing. Thus, mobility was found to be further enhanced by annealing.

TABLE 1

| | N/In signal ratio |
|---|---|
| Example 21 | $6 \times 10^{-5}$ |
| Example 22 | $8 \times 10^{-5}$ |
| Example 23 | $6 \times 10^{-5}$ |
| Example 24 | $6 \times 10^{-5}$ |
| Example 25 | $6 \times 10^{-5}$ |
| Comp. Ex. 2 | $4 \times 10^{-5}$ |

The invention claimed is:

1. A nitriding treatment liquid consisting of an alkali metal amide dissolved in a solvent, wherein the alkali metal amide is lithium amide, sodium amide, potassium amide, or a mixture thereof, and wherein the solvent comprises a cyclic alkylene urea represented by the following formula (1):

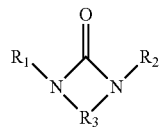

(1)

wherein each of $R_1$ and $R_2$ represents a C1 to C3 alkyl group, and $R_3$ represents a C1 to C4 alkylene group.

2. A nitriding treatment liquid according to claim 1, wherein the cyclic alkylene urea is dimethylpropylene urea or dimethylethylene urea.

3. A method for producing a nitrided metal oxide, wherein the method comprises a nitriding step of heating a nitriding treatment liquid as recited in claim 1 in an inert gas atmosphere, while the liquid is in contact with the surface of a metal oxide.

4. A nitrided metal oxide production method according to claim 3, wherein the method further includes, after the nitriding step, an annealing step of annealing the metal oxide which is treated by heating in a deoxygenated atmosphere.

5. A nitrided metal oxide production method according to claim 3, wherein the metal oxide is one species selected from $In_2O_3$, $Ga_2O_3$, $Al_2O_3$, $TiO_2$, $Fe_2O_3$, $MnO_2$, $WO_3$, $MoO_3$, $LizTiO_3$, $LizZrO_3$, $LizMoO_4$, $Li_2WO_4$, $Na_2MoO_4$, $LiGaO_2$, $LiInO_2$, $NaGaO_2$, $FeMoO_4$, $MnMoO_4$, $FeWO_4$, $MnWO_4$, $LiInO_2$, and $NaInO_2$, or a mixture of the plurality of the oxides.

6. A nitrided metal oxide production method according to claim 3, wherein the metal oxide is in the form of indium oxide film formed on a substrate.

* * * * *